United States Patent [19]

Itoh et al.

[11] Patent Number: 5,006,646

[45] Date of Patent: Apr. 9, 1991

[54] PROCESS FOR PREPARING 2'-DEOXY-5-TRIFLUOROMETHYL-BETA-URIDINE

[75] Inventors: Kazuo Itoh; Yoshitake Naoi, both of Tokyo; Hajime Matsushita, Kanagawa; Takashi Ebata, Kanagawa; Hiroshi Kawakami, Kanagawa, all of Japan

[73] Assignees: Yuki Gosei Kogyo Co., Ltd.; Japan Tobacco Co., both of Tokyo, Japan

[21] Appl. No.: 484,974

[22] Filed: Feb. 20, 1990

[30] Foreign Application Priority Data

Feb. 22, 1989 [JP] Japan ................... 1-40156

[51] Int. Cl.$^5$ ............................ C07H 1/00
[52] U.S. Cl. ............................... 536/23
[58] Field of Search ........................ 536/23

[56] References Cited

U.S. PATENT DOCUMENTS

| | | | |
|---|---|---|---|
| 4,092,472 | 5/1978 | Townsend et al. | 536/55 |
| 4,211,773 | 7/1980 | Lopez et al. | 536/23 |
| 4,352,795 | 10/1982 | Cook | 536/24 |
| 4,760,137 | 7/1988 | Robins et al. | 536/24 |
| 4,898,936 | 2/1990 | Ollmann et al. | 536/23 |
| 4,914,028 | 3/1990 | Hertel et al. | 536/26 |

FOREIGN PATENT DOCUMENTS 0136693 4/1985 European Pat. Off. .
0272065 6/1988 European Pat. Off. .
7901068 12/1979 PCT Int'l Appl. .

OTHER PUBLICATIONS

Lawlor et al., Chemical Abstracts vol. 99: 97963g, (1983).
Bardos T. J. et al, Tetrahedron Letters, No. 16, 1966 pp. 1759-1764 "Stereoselective Synthesis of Anomeric 5-Mercapto-2-Deoxyuridines".
The Synthesis of 2-Deoxy-5-Trifluoromethyl uridine utilizing a coupling reaction; Kawakami et al.; Heterocycles, vol. 31; No. 3, 1990; pp. 569-574.

Primary Examiner—Johnnie R. Brown
Assistant Examiner—James O. Wilson
Attorney, Agent, or Firm—Beveridge, DeGrandi & Weilacher

[57] ABSTRACT

The present invention is a process for preparing 2'-deoxy-5-trifluoromethyl-β-uridine characterized in that a 5-trifluoromethyl-2,4-bis(triorganosilyloxy)pyrimidine and a 1-halogeno-2-deoxy-α-D-erythro-pentofuranose derivative are subjected to condensation reaction in chloroform to give a 1-(2-deoxy-β-D-erythro-pentofuranoxyl)-5-trifluoromethyluracil derivative which is then subjected to the deprotection reaction to give 2'-deoxy-5-trifluoromethyl-β-uridine.

2 Claims, No Drawings

PROCESS FOR PREPARING 2'-DEOXY-5-TRIFLUOROMETHYL-BETA-URIDINE

BACKGROUND OF THE INVENTION (1) Field of the Invention

The present invention relates to a process for preparing 2'-deoxy-5-trifluoromethyl-β-uridine which is useful per se as a carcinostatic agent and is a raw material of other pharmaceutically useful compounds.

(2) Description of the Related Arts

2'-deoxy-5-trifluoromethyl-β-uridine is useful per se as a carcinostatic agent and is a raw material of other pharmaceutically useful compounds, and thus the demand thereof is increasing.

In the conventional process for preparing 2'-deoxy-5-trifluoromethyl-β-uridine, there are known the following methods:

(a) a method for transforming the nucleic base from thymidine and 5-trifluoromethyluracil with an enzyme such as nucleoside-2'-deoxyribose transferase [Methods Carbohydr. Chem., 7, 19 (1976)];

(b) a method as a chemical synthesis of preparing an anomeric mixture by the condensation of a 5-trifluoromethylurasil derivative and a 2-deoxy-D-erythro-pentofuranose derivative in the presence of a catalyst and isolating the β-isomer as the aimed product [J. Org. Chem., 31, 1181 (1966); U.S. Pat. No. 3531464]; and (c) a method of halogenating the 5-position of 2'-deoxy-β-uridine as a raw material and then subjecting the halogenated product to trifluoromethylation [J. Chem. Soc. Perkin Trans. I, 2755, 1980].

However, the aforementioned production methods have the following defects:

The production method (a) is not suited for a large scale production because of the problems of the isolation of the aimed product or the productivity; a harmful mercury salt is used and complicated and tedious operations are needed for isolating the β-isomer as the aimed product from the anomeric mixture in the production method (b); and 2'-deoxy-β-uridine as a raw material is expensive in the production method (c).

Thus, none of the methods (a)–(c) is suitable for the industrial production method.

Therefore, a process for preparing 2'-deoxy-5-trifluoromethyl-β-uridine suitable for industrial production has been desired in which the aforementioned problems in the conventional methods have been solved and a large amount of the product can be easily supplied.

SUMMARY OF THE INVENTION

We have conducted researches on the process for preparing selectively and efficiently the β-isomer represented by the following formula (I) without problems described above. As the result, we have found that the condensation reaction of the compound (III) and the compound (IV) proceeds with a selectivity of 90% or more to the β-isomer and with a high yield, and after the product is purified, the deprotection reaction of the thus purified compound (II) gives the compound (I). The present invention has been thus accomplished.

In other words, the present invention is a process for preparing 2'-deoxy-5-trifluoromethyl-β-uridine represented by the formula (I)

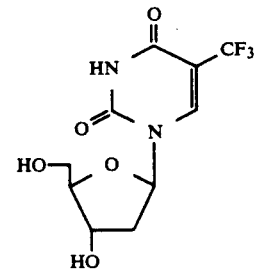

characterized in that a 5-trifluoromethyl-2,4-bis(triorganosilyloxy)pyrimidine represented by the general formula (IV)

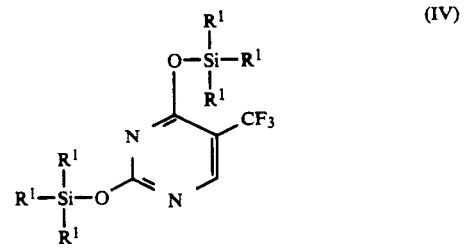

(wherein $R^1$ represents an alkyl group which may be substituted or a phenyl group) and a 1-halogeno-2-deoxy-α-D-erythro-pentofuranose derivative represented by the general formula (III)

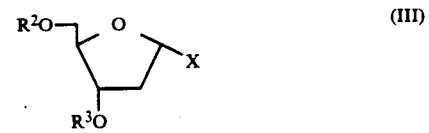

(wherein $R^2$ and $R^3$ represent a general protective group of a hydroxyl group, and X represents a halogen atom) are subjected to condensation reaction in chloroform to give a 1-(2-deoxy-β-D-erythro-pentofuranosyl)-5-trifluoromethyluracil derivative represented by the general formula (II)

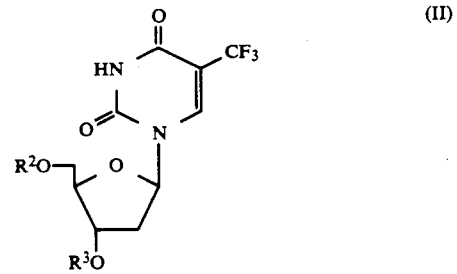

(wherein $R^2$ and $R^3$ represent a general protective group of a hydroxyl group) which is then subjected to the deprotection reaction to give 2'-deoxy-5-trifluoromethyl-β-uridine.

DESCRIPTION OF THE PREFERRED EMBODIMENTS

The compound (IV) as one of the raw materials of the present invention is obtained by the silylation of 5-tryfluoromethyluracil as described in J. Org. Chem., 31, 1181 (1966) and U.S. Pat. No. 3531464.

5-trifluoromethyluracil is commercially available and is described by Heidenberger et al. [J. Med. Chem., 7, 1 (1964)] or by Fuchigami et al. [Tetrahedron Lett., 23, 4099 (1982)].

The triorganosilyl group of the compound (IV) includes general protective groups of a hydroxyl group such as a trimethylsilyl group, a t-butyldimethyl silyl group, a phenyldimethylsilyl group or the like without limit thereto.

The compound (III) as another raw material of the present invention is prepared, for example, by the method described by Fox et al. [J. Am. Chem. Soc., 83, 4066 (1961)].

The protective groups of the two hydroxyl groups in the compound (III) include those which are generally used as a protective group of saccharides, for example, aralkyl groups such as benzyl, trityl and the like; acyl groups such as acetyl, propionyl, pivaloyl, benzoyl and the like; alkyloxycarbonyl groups such as ethoxycarbonyl and the like; and aryloxycarbonyl groups such as phenoxycarbonyl and the like without limit thereto. When the protective groups have a phenyl group, they may have as a substituent thereof an alkyl group, a halogen atom, a nitro group, an alkoxy group or the like.

The condensation reaction of the compound (IV) and the compound (III) is performed in an appropriate solvent, preferably in halogen containing hydrocarbons, more preferably in chloroform at an ambient temperature and is completed generally within 15 hours.

The condensation reaction can be carried out in the presence of a catalyst such as a Lewis acid (e.g., 15% by mole of zinc chloride) or in the absence of the Lewis acid catalyst.

The molar ratio of the compound (III) and the compound (IV) in the condensation reaction is in the range of 1:1–1:10, preferably 1:4.

The reaction mixture thus obtained is crystallized to give the purified $\beta$-isomer of the compound (II).

The product is then subjected to the deprotection reaction with hydrolysis, alkolysis, ammonolysis or the like to give 2'-deoxy-5-trifluoromethyl-$\beta$-uridine.

EXAMPLES

The present invention will be ilustrated by reference of the following examples.

In this connection, in all of the examples, 5-trifluoromethyl-2,4-bis(trimethylsilyloxy)pyrimidine was obtained by the silylation of a commercially available 5-trifluoromethyluracil, and 1-chloro-2-deoxy-3,5-di-O-(p-chlorobenzoyl)-$\beta$-D-erythro-pentofuranose was obtained by the method described by the aforementioned Fox et al. [J. Am. Chem. Soc., 83, 4066 (1961)].

EXAMPLE 1

Synthesis of
1-[2-deoxy-3,5-di-O-(p-chlorobenzoyl)-$\beta$-D-erythropentofuranosyl]-5-trifluoromethyluracil To a solution of 3.89 g (12.0 mmol) of 5-trifluoromethyl-2,4-bis(trimethylsilyloxy)pyrimidine in 24 ml of chloroform was added 60 mg (0.44 mmole) of zinc chloride as a Lewis acid catalyst under a dry condition. Next, 1.25 g (2.91 mmole) of 1-chloro-2-deoxy-3,5-di-O-(p-chlorobenzoyl)-$\alpha$-D-erythropentofuranose in the form of dry powder was added to the mixture, and the reaction mixture was stirred at an ambient temperature for 15 hours.

After the reaction was completed, the reaction solution was poured into an aqueous sodium hydrogen carbonate solution and extracted with chloroform. The organic layer was dried over anhydrous magnesium sulfate, and the solvent was evaporated under reduced pressure.

The residue thus obtained was crystallized from ethanol to give 1.34 g of the title compound (yield 80%).

Melting point: 173°–176° C.; $^1$H-NMR(CDCL$_3$): $\delta$ 8.05(s, 1H, H-6), 7.99(d, J=8.7 Hz, 1H, aromatic H), 7.92(d, J=8.7 Hz, 1H, aromatic H), 7.46(d, J=8.7 Hz, 1H, aromatic H), 7.43(d, J=8.7 Hz, 1H, aromatic H), 6.30(dd, J=8.3 and 5.5 Hz, 1H, H-1'), 5.61(d, J=6.6 Hz, 1H, H-3'), 4.74(d, J=3.7 Hz, 2H, H-5'), 4.61(dd, J=5.9 and 3.6 Hz, 1H, H-4'), 2.88(ddd, J=14.5 and 5.6 and 1.6 Hz, 1H, H-2'), 2.31(ddd, J=14.7 and 8.0 and 6.7 Hz, 1H, H-2").

Synthesis of 2'-deoxy-5-trifluoromethyl-$\beta$-uridine

To a solution of 1.32 g (2.30 mmole) of 1-[2-deoxy-3,5-di-O-(p-chlorobenzoyl)-$\beta$-D-erythro-pentofuranosyl]-5-trifluoromethyluracil in 80 ml of methanol was added 0.16 g (3.0 mmole) of sodium methoxide, and the mixture was stirred at an ambient temperature for 1 hour.

After completing the reaction, a pyridinium type cation exchange resin was added to the reaction solution, and stirring was conducted for 10 minutes to neutralize the solution.

After the resin was removed by filtration, the solvent was concentrated under reduced pressure, and the resulting residue was dissolved in water and washed twice with chloroform. The residue obtained by concentrating under reduced pressure the aqeous layer was purified by silica gel column chromatography (chloroform:methanol=85:15), and the resulting crystals were subjected to recrystallization from ethanol to give 458 mg of the title compound (yield 67%).

Melting point: 177°–179° C. (lit.: 186°–189° C.), $^1$H-NMR(CD$_3$OD): $\delta$ 8.81(s, 1H, H-6), 6.24(t, J=6.2 Hz, 1H, H-1'), 4,41(dt, J=5.9 and 4.1 Hz, 1H, H-3'), 3.96(dd, J=6.4 and 2.9 Hz, 1H, H-4'), 3.84(dd, J=11.9 and 2.8 Hz, 1H, H-5'), 3.74(dd, J=11.9 and 2.8 Hz, 1H, H-5"), 2.37(ddd, J=13.7 and 6.3 and 4.4 Hz, 1H, H-2'), 2.27(dq, J=13.1 and 6.2 Hz, 1H, H-2").

EXAMPLE 2

Synthesis of
1-[2-deoxy-3,5-di-O-(p-chlorobenzoyl)-$\beta$-D-erythropentofuranosyl]-5-trifluoromethyluracil To a solution of 12.9 kg (39.7 mole) of 5-trifluoromethyl-2,4-bis(trimethylsilyloxy)pyrimidine in 210 litre of chloroform was added 32.9 g (0.24 mmole) of zinc chloride under a dry condition. Next, 10.5 kg (24.4 mole) of 1-chloro-2-deoxy-3,5-di-O-(p-chlorobenzoyl)-$\alpha$-D-erythro-pentofuranose in the form of dry powder was added to the mixture, and the reaction mixture was stirred at an ambient temperature for 5.5 hours.

After the reaction was completed, the reaction solution was treated in the same manner as in Example 1 to give 10.4 kg of the title compound (yield 74%).

EXAMPLE 3

Condensation reaction in the absence of a Lewis acid catalyst

Under a dry condition, 2.5 mmole of 5-trifluoromethyl-2,4-bis(trimethylsilyloxy)pyrimidine as the compound (IV) was added to 7.5 ml of chloroform. Then, a suspension of a predetermined amount of 1-chloro-2-deoxy-3,5-di-O-(p-chlorobenzoyl)-α-D-erythro-pentofuranose as the compound (III) in the form of dry powder in 5 ml of chloroform was added with stirring to the mixture, and the reaction mixture was stirred at an ambient temperature for about 20 hours.

The amount of the compound (III) was adjusted depending on the molar concentration (0.2 mole/liter) of the compound (IV) to ensure that the molar ratio of the compound (III): the compound (IV) is in the range of 1:1–1:4.

Then, the reactions (Nos. 1–4) were carried out with various amounts of the compound (III).

After the reaction was completed, the reaction solution was subjected to HPLC determination to obtain the analytical yield of the α-isomer + β-isomer and the selectivity represented by the molar ratio of α-isomer:β-isomer.

Results are shown in the following table.

TABLE

|  | Molar ratio (III):(IV) | Analytical yield (%) | Selectivity α-isomer:β-isomer |
|---|---|---|---|
| No. 1 | 1:1 | 100 | 10:90 |
| No. 2 | 1:2 | 100 | 7:93 |
| No. 3 | 1:3 | 100 | 4:96 |
| No. 4 | 1:4 | 100 | 3:97 |

What we claim is:

1. A process for preparing 2'-deoxy-5-trifluoromethyl-β-uridine represented by the formula (I)

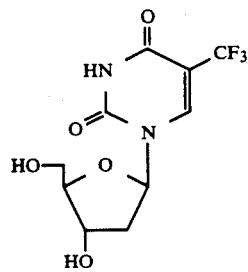

which comprises condensing:

a 5-trifluoromethyl-2,4-bis(triorganosilyloxy)pyrimidine represented by the formula (IV)

(IV)

(wherein $R^1$ represents an alkyl group, a substituted alkyl group or a phenyl group)

and a 1-halogeno-2-deoxy-α-D-erythro-pentofuranose derivative represented by the formula (III)

(III)

(wherein $R^2$ and $R^3$ represent a protective group of a hydroxyl group, and X represents a halogen atom) in chloroform to give a 1-(2-deoxy-β-D-erythro-pentofuranosyl)-5-trifluoromethyluracil derivative represented by the formula (II)

(II)

(wherein $R^2$ and $R^3$ represent a protective group of a hydroxyl group) which is then subjected to the deprotection reaction to give 2'-deoxy-5-trifluoromethyl-β-uridine.

2. A process for preparing 2'-deoxy-5-trifluoromethyl-β-uridine according to claim 1, wherein the condensation reaction is carried out in the presence of zinc chloride as a catalyst.

* * * * *